(12) United States Patent
Callaghan et al.

(10) Patent No.: US 9,198,795 B2
(45) Date of Patent: Dec. 1, 2015

(54) IMPLANT DELIVERY DEVICE

(71) Applicant: HOLOGIC, INC., Marlborough, MA (US)

(72) Inventors: David J. Callaghan, Mansfield, MA (US); Jeffrey Model, Cambridge, MA (US); Matthew LaPlaca, Cumberland, RI (US)

(73) Assignee: HOLOGIC, INC., Marlborough, MA (US)

( * ) Notice: Subject to any disclaimer, the term of this patent is extended or adjusted under 35 U.S.C. 154(b) by 340 days.

(21) Appl. No.: 13/784,661

(22) Filed: Mar. 4, 2013

(65) Prior Publication Data

US 2013/0239975 A1    Sep. 19, 2013

Related U.S. Application Data

(63) Continuation of application No. 12/646,317, filed on Dec. 23, 2009, now abandoned.

(51) Int. Cl.
*A61F 6/22* (2006.01)
*A61F 6/06* (2006.01)
*A61B 18/14* (2006.01)
*A61B 19/00* (2006.01)

(52) U.S. Cl.
CPC . *A61F 6/225* (2013.01); *A61F 6/06* (2013.01); *A61B 18/14* (2013.01); *A61B 19/54* (2013.01)

(58) Field of Classification Search
CPC combination set(s) only.
See application file for complete search history.

(56) References Cited

U.S. PATENT DOCUMENTS

| | | | |
|---|---|---|---|
| 4,900,303 A | 2/1990 | Lemelson | |
| 6,309,384 B1 * | 10/2001 | Harrington et al. | 606/28 |
| 6,544,236 B1 | 4/2003 | Cragg et al. | |
| 7,220,259 B2 | 5/2007 | Harrington et al. | |
| 2002/0183826 A1 | 12/2002 | Dorn et al. | |
| 2002/0188247 A1 | 12/2002 | Peery | |
| 2003/0229384 A1 * | 12/2003 | Mon | 607/96 |
| 2004/0255958 A1 | 12/2004 | Harrington et al. | |
| 2009/0266366 A1 | 10/2009 | Swann et al. | |
| 2010/0312223 A1 * | 12/2010 | Kozak et al. | 604/528 |

OTHER PUBLICATIONS

International Search Report and Written Opinion, forms PCT/ISA/210 and PCT/ISA/237, mailed Mar. 7, 2011, for PCT/US10/61598, Applicant Hologic, Inc., filed Dec. 21, 2010, 7 pages.

* cited by examiner

*Primary Examiner* — Ophelia A Hawthorne
(74) *Attorney, Agent, or Firm* — Vista IP Law Group LLP

(57) ABSTRACT

Devices and methods are disclosed for the delivery of a compressible implant into a bodily lumen. The delivery device includes an enlarged section that is configured to house the implant during delivery thereof into a patient. In certain embodiments, the implant is kept within the delivery device in a substantially uncompressed configuration prior to the delivery thereof.

14 Claims, 2 Drawing Sheets

IMPLANT DELIVERY DEVICE

RELATED APPLICATION DATA

This application is a continuation of pending U.S. patent application Ser. No. 12/646,317, filed Dec. 23, 2009, the priority of which is claimed under 35 U.S.C. §120, and the contents of which are incorporated herein by reference as though set forth in full.

FIELD OF THE INVENTION

The present invention relates to devices that are useful for the delivery of compressible implants into a bodily lumen, and more particularly, to devices that may be used to deliver a compressible implant into a fallopian tube.

BACKGROUND

It is often desired or necessary for medical reasons to deliver an implant into a bodily lumen, such as a lumen within the vascular, urogenital, and gastrointestinal systems. For example, stents may be delivered into any of these systems, embolic implants may delivered into blood vessels, and occlusion implants may be delivered into the fallopian tubes for sterilization purposes.

An example of an occlusive implant that is placed within the fallopian tubes for sterilization purposes is the Adiana® Permanent Contraception system (Hologic, Inc., Marlborough, Mass.). To use this system, a flexible delivery catheter is passed through the vagina and cervix and into each fallopian tube to deliver a low level of radiofrequency energy, followed by the delivery of a small, compressible occlusion implant. Implants are usually placed in the uterotubal junction, the narrowest part of the fallopian tubes. Such implants and procedures are described, for example, in U.S. Pat. No. 7,220,259, which is incorporated herein by reference.

Compressible implants, including occlusion implants, embolics, and stents, are often made from polymeric materials that allow for the compression of these implants into small profiles so that they may fit within the dimensions of their respective delivery devices. After the delivery device is positioned to a target location within the bodily lumen, the implant is extruded or otherwise released from the delivery device such that it self-expands from its reduced, delivery configuration into its intended expanded, working configuration. The expanded configuration may be necessary, for example, to apply forces against the surrounding bodily lumen wall to thereby keep the implant at the target location within the body.

Because many compressible implants are loaded into a delivery device at the point of manufacture rather than at the point of use, they are consequently kept in a reduced configuration within the confines of the delivery device during sterilization, shipping, and storage. During such time, the materials used in such compressible implants may undergo stress relaxation or other changes to mechanical properties that result from being held in a reduced configuration. If kept in the reduced configuration for too long and/or at elevated temperatures, the implant may not expand to a proper working configuration once released from its delivery device. The result is that many compressible implants have a short permissible shelf life and temperature exposure limitations.

It is an object of the present invention to provide for delivery devices and associated methods that allow for compressible implants to be sterilized, shipped, and stored for extended periods of time and/or at elevated temperatures without adversely affecting their properties or working function.

SUMMARY OF THE INVENTION

In one aspect, the present invention comprises a device for the delivery of a compressible implant into the body of a patient.

In another aspect, the present invention comprises a kit that includes a compressible implant pre-loaded in a delivery device.

In yet another aspect, the present invention comprises a method of treating a patient by delivering a compressible implant into the body of a patient by using the delivery devices of the present invention.

In certain embodiments, the present invention includes a device for the delivery of a compressible implant into the body of a patient. The delivery device comprises a proximal section, a distal section, and an intermediate section between the proximal and distal sections. Each of the proximal, distal, and intermediate sections comprise an inner dimension and an outer dimension and a continuous open space extending within their inner dimensions. The device includes an opening in the proximal section and another opening in the distal section, each of which provides access to the continuous open space. The inner and outer dimensions of the distal section are both less than the respective inner and outer dimensions of the intermediate section. The intermediate section is configured to house the compressible implant prior to its delivery, during which time a cross-sectional dimension of the compressible implant is greater than the inner dimension of the distal section. The device further includes a contact member configured to contact the compressible implant within the intermediate section, and to apply a force to the compressible implant so that it moves from the intermediate section into the distal section and through the opening in the distal section.

DESCRIPTION OF THE PREFERRED EMBODIMENTS

The present invention provides for the delivery of compressible implants using delivery devices that allow such implants to be kept in a substantially uncompressed configuration prior to delivery into a patient. Because the compressible implants are kept in a substantially uncompressed configuration, they can be sterilized, shipped and stored for relatively long time periods and at high temperatures while maintaining the ability to expand to a proper working configuration once delivered into a patient. In contrast, compressible implants that are sterilized, shipped and stored in substantially compressed configurations within the confines of conventional implant delivery devices have short permissible shelf lives and temperature exposure limitations in order to minimize the risk that they will undergo stress relaxation prior to delivery into a patient, and therefore not expand to acceptable working configurations.

The present invention is described with specific reference to an occlusive implant that is placed within the fallopian tubes for sterilization purposes. It should be recognized, however, that the devices and methods of the present invention are equally applicable to any compressible implant that must be compressed to facilitate delivery into a patient and then expand into a proper working configuration. Non-limiting examples of such implants include self-expanding polymeric stents, filters, and polymeric embolics and other occlusive implants.

Figures 1A, 1B:
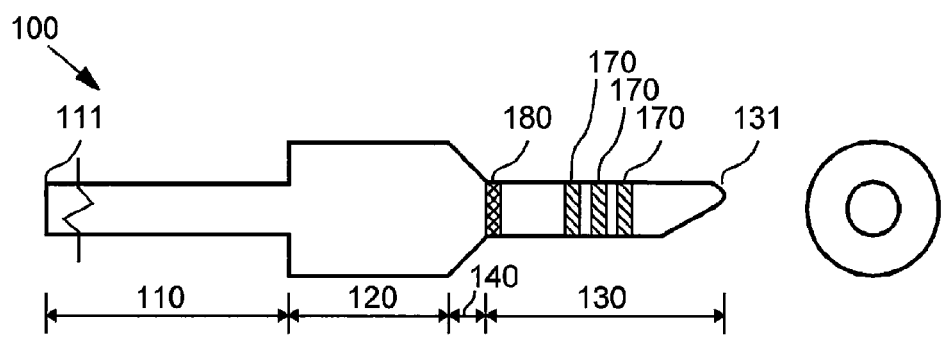
FIG. 1a is a side view, and FIG. 1b an end view, of a delivery device in accordance with an embodiment of the present invention.

In one embodiment, the present invention includes a device for the delivery of a compressible implant into a bodily lumen. As shown in the side view of FIG. 1a, the delivery device 100 generally comprises a proximal section 110, a distal section 130, and an intermediate section 120 between the proximal and distal sections 110, 130. The distal section 130 is intended to be insertable into the bodily lumen, and terminates in a distal tip 131. The proximal section 110 terminates in a proximal end 111, which is intended to extend outside of the body during use. As shown in the end view of FIG. 1b, the outer configuration of delivery device 100 and its sections are preferably cylindrical.

Figure 2:
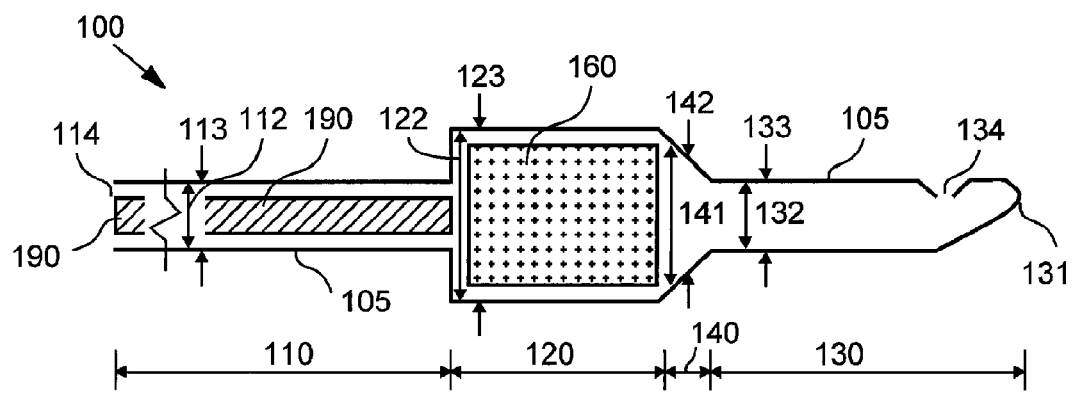
FIG. 2 is a cross-sectional view of a delivery device in accordance with an embodiment of the present invention.

As seen in cross section in FIG. 2, each of the proximal, distal, and intermediate sections 110, 130, 120 is characterized by a respective inner dimension, preferably a diameter, noted as dimensions 112, 132, and 122. Each section is also characterized by a respective outer dimension 113, 133, and 123, preferably a diameter, the size of which is sum of each respective inner dimension 112, 132, and 122 and twice the width of the side wall 105 of each respective section. In all embodiments of the invention, the inner and outer dimensions 132, 133 of the distal section 130 are less than the respective inner and outer dimensions 122, 123 of the intermediate section 120. In addition, the inner dimension of the proximal section 112 is preferably less than the inner dimension of the intermediate section 122. The outer dimension of the proximal section 113 may be less than the outer dimension of the intermediate section 123, as shown in FIGS. 1 and 2, or is preferably about the same size as the outer dimension of the intermediate section 123.

The delivery device 100 preferably includes a transition section 140 extending between the intermediate section 120 and the distal section 130. The transition section 140 is characterized by inner and outer dimensions 141, 142 that preferably gradually decrease from the respective inner and outer dimensions 122, 123 of the intermediate section to the respective inner and outer dimensions 132, 133 of the distal section.

The delivery device 100 includes an opening 114 in the proximal section, and another opening 134 in the distal section to provide access to a continuous open space 150 that extends within the inner diameters of the proximal, distal, and intermediate sections. While the opening 134 is preferably on a side wall of the distal section 130 as shown in FIG. 2, it is alternatively located at the tip of the distal end 131. Locating the opening 134 on the side wall instead of the tip of the distal end 131 allows the tip to be rounded, or preferably in the form of a "ball tip" to minimize trauma to tissue as the delivery device 100 is advanced through tissue or within a bodily lumen. The opening 114 in the proximal section allows for the loading of a compressible implant 160 into the delivery device 100, while the opening 134 in the distal section allows for the delivery of the compressible implant 160 into the patient.

Figure 3:
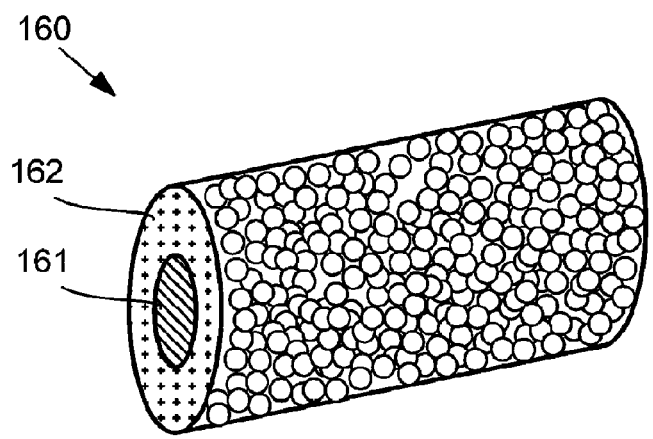
FIG. 3 is an occlusive implant that may be delivered into a patient, using the delivery devices of the present invention.

In the embodiment shown in FIG. 2, the compressible implant 160 is an occlusive implant that is intended to be placed within the fallopian tubes for sterilization purposes. In a preferred embodiment, the implant 160 comprises an inner core 161 and an outer porous portion 162 to form a porous plug, as shown in FIG. 3. The inner core and outer porous portion 161, 162 comprise any suitable material, such as silicone. The cross-sectional shape of the implant 160 may be round, oval, or any other suitable shape. In a preferred embodiment, the implant 160 is cylindrical and has an uncompressed diameter of between about 1.0 mm and 2.0 mm, preferably about 1.6 mm. The diameter of the inner core 161 is preferably between about 0.25 mm and 0.5 mm.

The outer porous portion 162 of implant 160 is preferably formed as a reticulated foam having an interconnected porous structure with a pore size in the range of 1-20 microns. The porous structure of the outer porous portion 162 contributes to the compressible nature of the implant 160 and helps to facilitate tissue ingrowth into the implant 160 following delivery into the patient. Silicone foam is preferred as the material for the outer porous portion 162, and may be formed using the procedure set forth in U.S. Pat. No. 5,605,693, which is incorporated herein by reference. In addition to silicone, examples of other materials that may be used to make the outer porous portion 162 include polytetrafluoroethylene (PTFE), acrylic copolymers, cellulose acetate, polyethylene (including HDPE), and polyester.

The intermediate section 120 of the delivery device 100 is configured to house the compressible implant 160 prior to delivery of the implant into the patient. The uncompressed diameter of the implant 160 is significantly larger than the inner diameter 132 of the distal section 130 of delivery device 100. According to preferred embodiments of the present invention, however, the uncompressed diameter of the implant 160 is about the same as, or slightly larger than, the inner diameter 122 of the intermediate section 120 such that the implant 160 remains in a substantially uncompressed configuration prior to its delivery into the patient. According to embodiments of the present invention, "substantially uncompressed configuration" means that the implant 160 is held within the inner diameter 122 of the intermediate section 120 to a dimension that is not less than about 70%, preferably not less than about 80%, more preferably not less than about 90%, and most preferably not less than about 95%, of its as-manufactured uncompressed diameter. It is preferred that the inner diameter 122 of the intermediate section 120 is at least marginally less than the uncompressed diameter of the implant 160 so that the implant is held in place by the walls of the intermediate section 120 during sterilization, shipping, and storage. It should be appreciated, however, that the present invention includes embodiments in which the inner diameter 122 of the intermediate section 120 is larger than the uncompressed diameter of the implant 160.

As non-limiting examples of dimensions of various aspects of the present invention, for a compressible implant having a diameter of about 1.6 mm, the length of the distal section 130 is about 10-15 mm to facilitate placement of the implant 160 into the uterotubal junction. The inner dimension 132 of the distal section is about 0.9 mm and the outer dimension 133 is about 1.1-1.4 mm. The inner dimension 122 of the intermediate section 120 is about 1.2-1.6 mm, and the outer dimension 123 is about 1.3-1.7 mm to facilitate introduction through a 5 French hysteroscope, as is described below.

The delivery device 100 preferably includes one or more electrodes, such as ring electrodes 170, mounted on the length of the distal section 130. Electrodes 170 are made from any suitable electrically conductive material such as stainless steel, copper, nickel-cobalt alloys, platinum, titanium, and nickel-titanium alloys. Electrodes 170 are configured for the delivery of radiofrequency (RF) energy or other suitable energy form, such as microwave energy, to surrounding tissue as part of a procedure that includes the delivery of implant 160 to the body of a patient. The energy may be supplied by any one of numerous energy generators available commercially.

The delivery device 100 also preferably includes a visual marker 180, such as a band optionally comprising a radiopaque material, placed around the distal section 130. Examples of radiopaque marker band materials include tungsten, gold, and platinum, as well as polymers that include barium sulfate, bismuth subcarbonate, bismuth trioxide, or bismuth oxychloride. The radiopaque marker 180 optionally includes one or more sensors to detect when the distal section 130 is in contact with tissue, as are known in the art. For example, the radiopaque marker 180 may include electrically conductive wires (not shown) that are in electrical connection with surrounding tissue and extend through the opening 114 in the proximal section 110. Current is passed through the wires, with a reduction in resistance indicating contact with tissue.

In the example of implant delivery for female sterilization, the compressible implant 160 is loaded into the intermediate section 120 of the delivery device 100 by insertion into the proximal section 110 using a funnel followed by advancing the implant using a push rod or similar instrument. In one embodiment, multiple compressible implants 160 are loaded into the intermediate section 120 for delivery into the body of a patient. The loaded delivery device is then packaged, sterilized using ethylene oxide gas, for example, and then shipped and stored until use. The inventors expect that the use of the delivery device of the present invention has the potential to increase the shelf life of an occlusive implant 160 to five years or longer.

When ready for use, the delivery device 100 is removed from its packaging materials and, in this example, is inserted through the vagina, through the cervix, and into the uterus. Such insertion may be done under x-ray guidance, sonographically, hysteroscopically, or in the absence of visualization, and may be conducted under general and/or local anesthesia. The transition section 140 is preferably sized such that it abuts the ostium of the fallopian tube such that the delivery device 100 cannot advance any further into the patient. The length of the distal section 130 is likewise sized so that the implant 160 is delivered to a desired location within the fallopian tube, given that the transition section 140 is in contact with the ostium. Once at this location, in a preferred embodiment, RF energy is delivered to the electrode(s) 170, which results in the ablation and consequent constriction of the tissue around the distal section 130.

Figure 4:
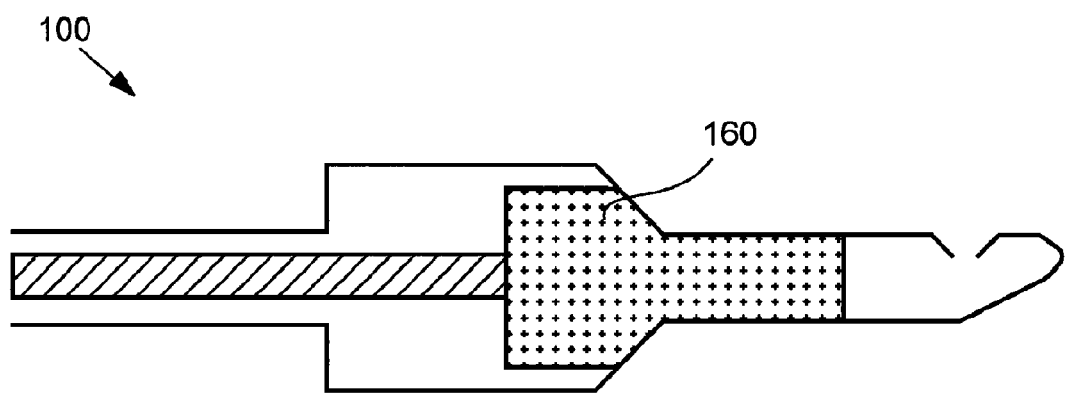
FIG. 4 is a cross-sectional view of a delivery device in accordance with an embodiment of the present invention in which a compressible implant is being advanced into a distal section of the delivery device.

Subsequent to tissue ablation, or alternatively in the absence of any tissue ablation, the implant 160 is extruded from the delivery device 100 by the relative movement between a contact member 190 and the delivery device 100. For example, the contact member 190 is inserted into the proximal section 110 to contact the implant 160 and push it into the distal section 130, as shown in FIG. 4. Alternatively, the contact member 190 is held stationary, and the delivery device 100 is withdrawn in a proximal direction such that the contact member forces the implant 160 to enter into the distal section 130. In either case, the implant 160 moves through the distal section 130 and exits the delivery device 100 through the opening 134 and into the patient. The contact member 190 is made from any suitable material that provides sufficient column stiffness to provide a force to the implant 160 such that it enters the distal section 130 and exits the opening 134. Examples of such materials include tubes or wires made from stainless steel or nitinol. In a preferred embodiment, the distal end of the contact member 190 is coated with polyurethane or other polymeric material to minimize the risk of damaging the implant 160 upon the application of force by the contact member 190.

The deployed implant 100 is left within the patient to provide permanent occlusion of the fallopian tube. The process is repeated for each fallopian tube. The implant 100 is maintained in place by the constrictive action of the surrounding tissue. As an aid to long term retention, the implant is porous as previously discussed to facilitate tissue ingrowth.

The delivery device 100 of the present invention is manufactured using known fabrication techniques and materials. For example, the delivery device 100 may be manufactured by extruding two polymeric tubes with flared and tapered ends, and then joining the flared ends to define the intermediate section 120. Such tubes may be made from any suitable material, such as, for example, polyurethane or polyether block amide such as PEBAX® (Arkema France Corporation, Colombes, France). In a preferred embodiment, an outer jacket of a relatively stiff material, such as polyetheretherketone, is applied over the proximal section 110, and preferably over the intermediate section 120, as an extrusion.

The present invention provides for the delivery of compressible implants using delivery devices that allow such implants to be kept in a substantially uncompressed configuration prior to delivery into a patient, and thereby enables an extended shelf life for such implants without severe temperature limitations. Although the present invention is described with specific reference to an occlusive implant that is placed within the fallopian tubes for sterilization purposes, it is intended that the present invention be applicable to any compressible implant that must be compressed to facilitate delivery into a patient and then expand into a proper working configuration. Furthermore, it will be apparent to those skilled in the art that various modifications and variations can be made in the structure and methodology of the present invention. It is intended that the present invention cover the modifications and variations of this invention provided that they come within the scope of the appended claims and their equivalents.

We claim:

1. A method of implanting a compressible occlusive device in a fallopian tube of a patient, the fallopian tube having an ostium, comprising:
    inserting a distal section of an introducer into the fallopian tube until the distal section is adjacent an implant location in the fallopian tube, and such that an intermediate section of the introducer is positioned outside of the fallopian tube adjacent the ostium;
    moving the occlusive device from the intermediate section of the introducer into the distal section, wherein the intermediate section has an intermediate section inner diameter, such that the occlusive device, when disposed in the intermediate section, is in a substantially uncompressed configuration, wherein, when the occlusive device is moved from the intermediate section to the distal section, the occlusive device passes through a transition section of the introducer that compresses the occlusive device; and
    deploying the occlusive device out a distal opening in the distal section of the introducer and into the fallopian tube at the implant location.

2. The method of claim 1, wherein the occlusive device has an uncompressed outer diameter.

3. The method of claim 2, wherein the intermediate section inner diameter is more than 70% of, and less than 100% of, the uncompressed outer diameter.

4. The method of claim 2, wherein the intermediate section inner diameter is more than 80% of, and less than 100% of, the uncompressed outer diameter.

5. The method of claim 2, wherein the intermediate section inner diameter is more than 90% of, and less than 100% of, the uncompressed outer diameter.

6. The method of claim 2, wherein the intermediate section inner diameter is more than 95% of, and less than 100% of, the uncompressed outer diameter.

7. The method of claim 1, further comprising ablating tissue in the fallopian tube at the implant location prior to deploying the occlusive device.

8. The method of claim 7, wherein ablating tissue in the fallopian tube comprises delivering RF energy to the tissue in the fallopian tube via the distal section of the introducer.

9. The method of claim 7, wherein ablating tissue in the fallopian tube at the implant location causes the tissue to constrict around the occlusive device after the occlusive device is deployed into the fallopian tube.

10. The method of claim 1, wherein moving the occlusive device comprises moving a pusher member in a distal direction relative to the introducer.

11. The method of claim 10, wherein deploying the occlusive device comprises moving the pusher member in a distal direction relative to the introducer.

12. The method of claim 10, wherein deploying the occlusive device comprises moving the introducer in a proximal direction relative to the pusher member.

13. The method of claim 1, wherein inserting the distal section of the introducer into the fallopian tube until the distal section is adjacent the implant location in the fallopian tube comprises inserting the distal section of the introducer into the fallopian tube until the intermediate section of the introducer abuts an ostium of the fallopian tube.

14. The method of claim 1, wherein the occlusive device is configured to expand after being deployed into the fallopian tube to thereby occlude the fallopian tube.

* * * * *